United States Patent
Mincheff et al.

(10) Patent No.: US 6,387,888 B1
(45) Date of Patent: May 14, 2002

(54) IMMUNOTHERAPY OF CANCER THROUGH EXPRESSION OF TRUNCATED TUMOR OR TUMOR-ASSOCIATED ANTIGEN

(75) Inventors: Milcho S. Mincheff, Rockville; Dmitri I. Loukinov; Serguei Zoubak, both of Germantown, all of MD (US)

(73) Assignee: American Foundation for Biological Research, Inc., Rockville, MD (US)

( * ) Notice: Subject to any disclaimer, the term of this patent is extended or adjusted under 35 U.S.C. 154(b) by 0 days.

(21) Appl. No.: 09/164,034

(22) Filed: Sep. 30, 1998

(51) Int. Cl.$^7$ .................. A61K 48/00; C12N 15/63; C12N 15/85; C07H 21/02

(52) U.S. Cl. .............. 514/44; 435/320.1; 435/325; 536/23.1; 536/23.5

(58) Field of Search .................. 514/44; 424/93.1

(56) References Cited

U.S. PATENT DOCUMENTS

| | | |
|---|---|---|
| 4,861,589 A | 8/1989 | Ju |
| 5,013,645 A | 5/1991 | Kim |
| 5,045,320 A | 9/1991 | Mescher |
| 5,227,471 A | 7/1993 | Wright, Jr. |
| 5,314,996 A | 5/1994 | Wright, Jr. |
| 5,538,866 A | 7/1996 | Israeli et al. |
| 5,580,859 A | 12/1996 | Felgner et al. |
| 5,589,466 A | 12/1996 | Felgner et al. |
| 5,660,834 A | 8/1997 | Kjeldsen et al. |
| 5,679,647 A | 10/1997 | Carson et al. |
| 5,693,622 A | 12/1997 | Wolff et al. |
| 5,738,852 A | 4/1998 | Robinson et al. |
| 5,773,215 A | 6/1998 | Hanausek-Walaszek et al. |
| 5,788,963 A | 8/1998 | Murphy et al. |
| 5,804,566 A | 9/1998 | Carson et al. |
| 5,807,978 A | 9/1998 | Kokolus et al. |
| 5,830,877 A | 11/1998 | Carson et al. |
| 5,849,719 A | 12/1998 | Carson et al. |
| 5,854,206 A | 12/1998 | Twardzik et al. |
| 5,925,362 A | 7/1999 | Spitler et al. |
| 5,935,818 A | 8/1999 | Israeli et al. |
| 5,985,847 A | 11/1999 | Carson et al. |
| 6,034,218 A | 3/2000 | Reed et al. |
| 6,224,870 B1 * | 5/2001 | Segal .................. 424/192.1 |

FOREIGN PATENT DOCUMENTS

| | | |
|---|---|---|
| WO | WO 92/09690 | 6/1992 |
| WO | WO 93/20185 | 10/1993 |
| WO | WO 94/28113 | 12/1994 |
| WO | WO 95/04548 | 2/1995 |

OTHER PUBLICATIONS

B Bodey et al.,Anticancer Research, "Failure of Cancer Vaccines: The Significant Limitations of this Approach to Immunotherapy," Review, (2000), 20:2665–2676.*

JM Specht et al., Journal of Experimental Medicine, "Dendritic Cells Retrovirally Transduced with a Model Antigen Gene Are Therapeutically Effective against Established Pulmonary Metastases," Oct. 1997, vol. 186, No. 8, pp. 1213–1221.*

A Ribas et al., Advances in Brief, "Genetic Immunization for the Melanoma Antigen MART–1/Melan–A Using Recombinant Adenovirus–transduced Murine Dendritic Cells 1," Cancer Research, Jul. 1997, 57, 2865–2869.*

SL Eck et al., The Pharmacological Basis of Therapeutics, "Gene–Based Therapy,"9th, Edition, 1995, Chap.5, pp. 77–101.*

Hiroshima (1996), Carbohydrate Antigens, *Recent Advances in Gastroenterological Carcinogenesis* 1996: 192–97.

Huang, A. Y. C. et al. (1994), Role of Bone Marrow–Derived Cellsin Presenting MHC Class I–Restricted Tumor Antigens, *Science* 264:961.

Apostolopoulos, V. et al. (1995), The immunogenicity of MUC1 peptides and fusion protein, *Cancer Letters* 90:21–26.

Ceriani, R.L. et al. (1992), Epitope expression on the breast epithelial mucin, *Breast Cancer Research and Treatment* 24:103–13.

Lewis, J.J. et al. (1995), Definition of tumor antigens suitable for vaccine construction, *Cancer Biology* 6:321–27.

Nguyen, P.L. et al. (1996), Membrane–Bound (MUC1) and Secretory (MUC2, MUC3, and MUC4) Mucin Gene Expression in Human Lung Cancer, *Tumor Biol.* 17:176–92.

Knight, S.C. et al. (1985), Influence of Dendritic Cells on Tumor Growth, *Proc. Natl. Acad. Sci. USA* 82:4495–97.

Kokontis, J. et al. (1994), Increased Androgen Receptor Activity and Altered c–myc Expression in Prostate Cancer Cells after Long–Term Androgen Deprivation, *Cancer Research* 54:1566–73.

(List continued on next page.)

Primary Examiner—Robert A. Schwartzman
Assistant Examiner—Janice Li
(74) Attorney, Agent, or Firm—Isabelle M. Clauss; Foley, Hoag & Eliot

(57) ABSTRACT

DNA constructs for truncated forms of cancer-specific or cancer associated antigens are included in plasmid or viral expression vectors. The rationale to use constructs for truncated and not for full-size molecules is to eliminate side effects (toxicity, signal transduction etc.) arising from expressed proteins and/or, in cases where such molecules are expressed on the membrane, secreted, or released in the extracellular environment, to prevent formation of antibodies against them. The extracellular portion of the human prostate specific membrane specific antigen (XC-PSMA) has been cloned. Patients were treated either by injection of DNA coding for XC-PSMA in a mammalian expression vector under the CMV promoter or/and by a replication-defective adenoviral vector (Ad5)hat contains an expression cassette for the XC-PSMA. In a third method dendritic cells are isolated from a patient and are treated by exposure to the plasmid or adenovirus used in the previous two treatments. The dendritic cells are then injected into the patient. In some patients, the progression of metastatic prostate cancer is retarded or stopped.

30 Claims, No Drawings

OTHER PUBLICATIONS

Santambrogio, L. et al. (1998), Altered peptide ligand modulation of experimental allergic encephalomyelitis: immune responses within the CNS, *J. of Neuroimmunology* 81:1–13.

Julius S. Horoszewicz, et al., "Monoclonal Antibodies to a New antigenic Marker in Epithelial Prostatic Cells and Serum of Prostatic Cancer Patients", Anticancer Research, 7:927–936 (1987).

Ruthe Luthi–Carter, et al., Molecular Characterization of Human Brain N–Acetylated α–Linked Acidic Dipeptidase (NAALADAse), The Journal of Pharmacology and Experimental Therapeutics, vol. 286, No. 2, Apr. 20, 1998, pp. 1020–1025.

Ron S. Israeli et al., "Expression of the Prostate–specific Membrane Antigen", Cancer Research 54, Apr. 1, 1994, pp. 1807–1811.

Frederic Dumas et al., "Molecular Expression of PSMA mRNA and Protein in Primary Renal Tumors", Int. J. Cancer; 80, 799–803 (1999).

He Liu Peggy Moy, et al., "Monoclonal Antibodies to the Extracellular Domain of Prostate–specific Membrane Antigen Also React with Tumor Vascular Endothelium", Cancer Research 57, Sep. 1, 1997, pp. 3629–3634.

Ruth E. Carter et al., Prostate–specific membrane antigen is a hydrolase with substrate and pharmacologic characteristics of a neuropeptidase, Proc. Natl. Acad. Sci. USA, vol. 93, Jan. 1996, pp. 749–753.

* cited by examiner

IMMUNOTHERAPY OF CANCER THROUGH EXPRESSION OF TRUNCATED TUMOR OR TUMOR-ASSOCIATED ANTIGEN

CROSS-REFERENCE TO RELATED APPLICATIONS

Not Applicable.

STATEMENT REGARDING FEDERALLY SPONSORED RESEARCH OR DEVELOPMENT

Not Applicable.

BACKGROUND OF THE INVENTION (1) Field of the Invention

The present invention relates to compositions and methods for immunotherapy of human cancer patients.

(2) Description of Related Art Including Information Disclosed Under 37 CFR 1.97 and 37 CFR 1.98.

All normal human nucleated cells express on their membrane small protein fragments derived from de novo protein synthesis. These so-called peptides are associated with the major histocompatibility complex (MHC) class I molecules and form the antigens which are recognized by CD8 cytotoxic T-lymphocytes (CTLs). Such recognition is important for the elimination of virally infected cells, of tumor cells, or of cells that contain intracellular parasites. For this to occur potentially antigen-reactive T cells need to be "pre-educated" by recognizing the antigen in question on the membrane of professional antigen-presenting cells (dendritic cells) (APCs, DCs) which, in addition to the antigen, provide co-stimulatory "maturation" signals to the T cells. In the absence of such signals the T cells become paralyzed and tolerant to the antigens in question.

Tumor cells, which are not professional APCs, do not stimulate CTL generation and are not rejected by the immune system. For the generation of an immune response against a tumor the tumor antigen(s) need(s) to be expressed by professional APCs. This presentation has been accomplished by in vitro exposure of dendritic cells to tumor lysates that presumably contain tumor antigens, to purified tumor antigens or, to peptides derived from such antigens.

Another possibility to achieve expression of antigen-derived peptides is by introducing into dendritic cell desoxy—(DNA) or ribonucleic acid (RNA) that encodes the antigen of interest. Cells transfected with the plasmid DNA transiently synthesize the protein and the peptides that are obtained during the synthesis are then expressed in association with MHC. For example, patient's cells grown in vitro are transfected with plasmids, containing the DNA, or with the RNA of interest or infected with a recombinant viral vector that contains the DNA or RNA, and then returned to the patient. Another possibility is to directly immunize the patient with the plasmid ("nude" DNA immunization) or with the recombinant viral vector.

A major problem with this technique comes from the possible adverse effects of the expressed products on the patient's health or on cell viability. Since the function of these tumor-associated or tissue-specific antigens is largely unknown, their synthesis and release by patient's cells in vivo may lead to serious side effects. Furthermore, in cases where dendritic cells are transfected in vitro, expression of a functional protein may alter dendritic cell viability, change their migration pattern or their ability to provide co-stimulation to T cells.

The present invention discloses the idea for the introduction of specific changes in the DNA or RNA encoding the antigen in question as a way of solving this problem. Such changes result in the expression of functionally inactive products without affecting the efficiency of transcription and translation of the DNA, the translation of the RNA, or the generation of antigenic peptides. Specifically the present invention discloses the development of a DNA, which leads to expression of a truncated form of the human prostate specific membrane antigen (PSMA). In particular, we have developed a DNA construct with deletions of the membrane and the intracellular portions of the human PSMA. The resulting DNA encoding the extracellular portion of the PSMA (XC-PSMA) has been incorporated in mammalian expression vectors. PSMA is a type II protein, it lacks a hydrophobic signal sequence and therefore is not secreted by the cell that produces it. Since our construct lacks membrane and cytoplasmic sequences, the resulting protein is not expressed on the membrane, therefore does not transduce signals and is not released from the membrane. Cells transfected with the XC-PSMA plasmid retain viability and express PSMA-derived peptides.

Furthermore, since the synthesized protein is not released but remains confined to the intracellular milieu, there is no production of antibodies directed against the protein and the immune response remains strictly cell-mediated. The exquisite engagement of cell-mediated immunity against a particular antigen is very important especially in cases where the target antigen of interest is expressed on normal tissues that are anatomically sequestered in immuno-privileged sites such as the eye, brain, testis etc. Those tissues are inaccessible to cell mediated injury, but readily damaged by antibodies. Immunotherapy based on eliciting cellular responses to differentiation (tyrosinase; gp100; TRP1; TRP2; MART-1/Melan-A; membrane-associated mucin, MUC-1 mucin) or normal tissue-specific (PSMA, PSA) antigens constitute an example where the production of antibodies against the target must not occur.

In the first method of treating of prostate cancer patients, the plasmid is injected intradermally. In a second method of treatment, the plasmid is incorporated into the genome of a replication-deficient adenovirus, which is injected intradermally into a patient. In a third method of treatment, CD14+ monocyte cells of a prostate cancer patient are isolated and matured into dendritic cells (DC) and transfected with either the plasmid or the adenovirus of the first two methods. The DC are then stimulated to express MHCs and are infused back into the prostate cancer patient where they stimulate autologous T-cells. These stimulated T-cells then destroy both normal and malignant prostate cells.

The effect of all of these treatments is to either by-pass the normal tolerance for self-antigens or the tolerance to tumor antigens. This will enable the cytolysis of target normal and malignant prostate cells normally shielded from immune recognition. The destruction of normal prostate cells by this procedure is not detrimental to the patient. A malignant prostate (with its mixture or normal and malignant cells) customarily is destroyed through surgery or radiation in the conventional primary treatment for this disease.

U.S. Pat. No. 5,227,471 discloses the structure of the prostate-specific membrane antigen. A method for treating prostate cancer was disclosed which involves an antibody directed against the prostate-specific membrane antigen and a cytotoxic agent conjugated thereto. However, since the PSMA is expressed on normal brain cells, use of antibodies which can transverse through the blood-brain barrier and damage normal brain cells is not acceptable. Methods for imaging prostate cancer and an immunoassay for measuring the amount of prostate-specific membrane antigen also were disclosed.

U.S. Pat. No. 5,788,963 discloses the use of human dendritic cells to activate T cells for immuno-therapeutic response against primary and metastatic prostate cancer. Human dendritic cells are isolated and exposed to PSMA or peptides derived thereof in vitro. The PSMA or peptides are believed to exchange with peptides already bound to MHC molecules on the dendritic cells and thereby to be expressed in an imunogenic manner, enabling the DC to stimulate killer cells which then lyse prostate cells.

U.S. Pat. Nos. 5,227,471 and 5,788,963 are incorporated by reference herein.

The present invention differs from the prior art in that it causes the DC to present an antigen derived from prostate cancer cells on their surface through transfection with a plasmid or adenovirus. The transfection may occur in vivo using injected plasmid or adenovirus. Alternatively, the transfection may occur in vitro using purified DC precursor cells isolated from the prostate cancer patient's blood. If transfection is done in vitro, the transformed cells are injected into the patient. Transfected DC cells are superior to DC cells, which have been exposed to antigen in vitro because both their loading with antigen-derived peptide and their ability to stimulate killer cells are more efficient. In addition, in vivo transfection using a plasmid or adenovirus is less laborious and less expensive than in vitro methods. The use of transfected cells avoids the necessity of identifying peptides capable of binding to different HLA phenotypes, as is required in methods, which involve the addition of peptides to cells. Finally, the use of a DNA sequence that encodes a truncated molecule of the PSMA guarantees that the protein is not released by the transfected cells and no antibodies against the target protein that are potentially hazardous to normal brain tissue are produced. The methods of the present invention bypass the normal tolerance for self-antigens. This enables the cytolysis of target cells normally shielded from immune recognition.

Another application involves treatment of melanoma patients. Melanocyte differentiation antigen MART-1 is a common melanoma antigen recognized by many CTLs from melanoma patients. It represents a membrane protein of 118 aminoacids and a single transmembrane domain. Either DNA encoding for a truncated form with no transmembrane domain or a full-size protein with no leading sequenceis included in a plasmid or viral expression vector and used for immunotherapy similar to the one described for prostate cancer patients.

Another application involves treatment of breast, ovary, uterine, prostate or lung cancer patients. Her-2/neu antigen is a member of the epidermal factor receptor family and is presumed to function as a growth receptor. It is a transmembrane protein and is expressed during fetal development and very weekly on normal cells as a single copy. Amplification of the gene and/or overexpression of the associated protein have been identified in many human cancers such as breast, ovary, uterus, stomach, prostate and lung. DNA encoding for a truncated form of the Her-2/neu protein lacking the transmembrane portion and the leading sequence is constructed and included in a plasmid or viral vector(s) and used for in vitro or in vivo modification of patient dendritic cells and for immunotherapy.

DETAILED DESCRIPTION OF THE INVENTION

The present invention discloses the idea for the construction of genetically modified forms of polynucleotides encoding either tissue-specific or tumor antigens and for the use of such constructs for immunotherapy of primary or metastatic cancer. The genetic modification of the constructs leads to expression of either functionally inactive products or prevents functionally active molecules from being secreted or expressed on the membrane of transfected cells. Such genetic modifications, however, do not affect the antigenicity of the expressed protein, its primary structure or the generation of peptides available for binding to cell's MHC molecules. The polynucleotide may be either a DNA or RNA sequence. When the polynucleotide is DNA, it can also be a DNA sequence, which is itself non-replicating, but is inserted into a plasmid, and the plasmid further comprises a replicator. The DNA may be a sequence engineered so as not to integrate into the host cell genome. The polynucleotide sequences may code for a polypeptide which is either contained within the cells or secreted therefrom, or may comprise a sequence which directs the secretion of the peptide.

The DNA sequence may also include a promoter sequence. In one preferred embodiment, the DNA sequence includes a cell-specific promoter that permits substantial transcription of the DNA only in predetermined cells. The DNA may also code for a polymerase for transcribing the DNA, and may comprise recognition sites for the polymerase and the injectable preparation may include an initial quantity of the polymerase.

In many instances, it is preferred that the polynucleotide is translated for a limited period of time so that the polypeptide delivery is transitory. The polypeptide may advantageously be a therapeutic polypeptide, and may comprise an enzyme, a hormone, a lymphokine, a receptor, particularly a cell surface receptor, a regulatory protein, such as a growth factor or other regulatory agent, or any other protein or peptide that one desires to deliver to a cell in a living vertebrate and for which corresponding DNA or mRNA can be obtained.

In preferred embodiments, the polynucleotide is introduced into muscle tissue; in other embodiments the polynucleotide is incorporated into tissues of skin, brain, lung, liver, spleen or blood. The preparation is injected into the vertebrate by a variety of routes, which may be intradermally, subdermally, intrathecally, or intravenously, or it may be placed within cavities of the body. In a preferred embodiment, the polynucleotide is injected intramuscularly. In still other embodiments, the preparation comprising the polynucleotide is impressed into the skin. Transdermal administration is also contemplated, as is inhalation.

One example of this approach is the use of a DNA that encodes a truncated form of the human PSMA, which lacks the membrane, and cytoplasmic portions of the molecule. Such DNA has been included by us into mammalian expression vectors: a plasmid and a propagation deficient virus.

For treatment of prostate cancer patients, dendritic cells are prepared by transfection using either a plasmid or a recombinant replication-deficient adenovirus whose DNA includes DNA encoding a truncated fragment of the prostate specific membrane antigen. Dendritic cells may be transfected in vivo by injection of plasmid or recombinant replication-deficient adenovirus in the patient. Alternatively the DC may be transfected (infected) in vitro by treating isolated dendritic cell precursor cells with plasmid (or recombinant replication-deficient adenovirus). The dendritic cells are then injected into the patient.

Without wishing to be held to this theory, it is the inventors' belief that successful immunotherapy requires that the target antigen be presented by a DC simultaneously to both the helper (CD4+ T cells) and the effector (CD8+ T cells) arms of the immune system. Recognition by CD4+ T cells requires that antigenic peptides be expressed in conjunction with class II MHC molecules on the DC surface. This can be achieved by in vivo or in vitro transfection of DC with plasmid or infection of DC with recombinant adenovirus, both of which carry the DNA for the extracellular fragment of PSMA.

PSMA expression is restricted to prostate epithelial cells (Horoszewicz J S, Kawinski E and Murphy G P. Monoclonal antibodies to a new antigenic marker in epithelial prostate cells and serum of prostate cancer patients. Anticancer Res. 7:927;1987) and human brain tissue (Luthi-Carter R, Barczak A K, Speno H, Coyle J T. Molecular characterization of human brain N-acetylated alpha-linked acidic dipeptidase (NAALADase). J Pharmacol. Exp. Therap. 286:1020;1998). The antigen is expressed on normal and neoplastic prostate cells in the prostate or in prostate tumor metastases. While other marker antigens for prostate carcinoma such as prostate acid phosphatase and the prostate specific antigen (PSA) are secreted antigens, PSMA is an integral membrane glycoprotein.

Cloning of extracellular fragment of PSMA cDNA of PSMA extracellular fragment (2118 bp) was obtained using total mRNA from the prostate tumor cell line LNCaP.FGC—CRL 1740 (ATCC). A PSMA-specific 3'-primer was used for reverse transcription of mRNA which was performed using RT from avian myeloblastosis virus (Boehringer). Th resulting cDNA was then amplified using High Fidelity PCR System (Boehringer), and the gel purified PCR product of expected length was cloned into pCR2.1 vector (Invitrogen). Two clones were selected and checked by DNA sequencing. The resulting construct contains a free of mutation extracellular portion of PSMA with NotI-Kozak sequence introduced by PCR at its 5' end and SfuiI site at its 3' end.

Preparation of the mammalian expression vector for subcloning of the extracellular portion of PSMA.

The modified cloning vector pcDNA3.1 (Invitrogen) was used for subcloning. The vector provides human cytomegalovirus (CMV) immediate-early promoter/enhancer region permitting efficient, high-level expression of recombinant protein as well as 3' flanking region containing bovine growth hormone polyadenilation signal for efficient transcription termination and for increasing the half life of the mRNA in vivo. The neomycin resistance gene (NRG) was removed by digestion with NaeI endonuclease and ligation of the NRG-free fragment of the plasmid following gel purification.

Subcloning of the extracellular portion of PSMA into a mammalian expression vector.

The extracellular fragment of the PSMA was sub-cloned into a modified mammalian expression vector pcDNA3.1 by NotI-SfuI cloning sites. Both NotI and SfuI sites as well as Kozak sequence were introduced during the RT-PCR step of the cloning.

Deposit of modified mammalian expression vector pcDNA3.1.

The modified mammalian expression vector was deposited as Designation Number 203168 on Aug. 28, 1998 at the American Type Culture Collection, 10801 University Blvd., Manassas, Va. 20110.

Preparation of a replication-defective recombinant adenovirus Ad5-PSMA.

Ad5-PSMA recombinant adenovirus was prepared using the kit available from Quantum Biotechnology Inc. The transfer vector was constructed by subcloning of the extracellular PSMA fragment into the plasmid pAdBN (Quantum). For this purpose the PSMA fragment was initially sub-cloned into an unmodified pCDNA3.1 vector (Invitrogen). The portion of the plasmid that contains the CMV promoter-PSMA fragment-PolyA signal was cut using BglII and SmaI restriction endonucleases. The resulting product was purified on an agarose gel and subcloned by BglII-EcoRV cloning sites into pAdBN transfer vector (Quantum Biotechnologies Inc., Montreal, Canada).

The transfer vector was linearized with ClaI and co-transfected with linearized Adenovirus DNA in 293A cells. The recombinant adenovirus was purified three times and clones that were positive for PSMA expression were selected by immunoblotting. The positive clone was amplified in 293 cells and then purified on two successive CsCl gradients. Finally the purified virus was dialyzed against PBS-5% sucrose.

The replication-defective recombinant adenovirus Ad5-PSMA. was deposited as Designation Number 203168 on Aug. 28, 1998 at the American Type Culture Collection, 10801 University Blvd., Manassas, Va. 20110.

In vitro experiments:

Gene Transfer Using Replication-Deficient Adenovirus.

Peripheral blood mononuclear cells (PBMC) from healthy anonymous donors were isolated from freshly drawn blood by density centrifugation on Ficol-Paque at 468 g at 22° C. for 30 minutes. PBMC were resuspended in RPMI with 5% autologous serum (complete medium) culture medium at $1 \times 10^6$ cells/ml and allowed to adhere onto 175 cm$^2$ polystyrene tissue culture flask. The flasks are incubated at 37° C. and shaken every 20 minutes during incubation. After 1 hrs at 37 C., non-adherent cells are removed and adherent cells are cultured in 30 ml medium containing 2 ng/ml granulocyte macrophage colony-stimulating factor GM-CSF) obtained from Immunex, Seattle, Wash. and 4 ng/ml interleukin-4 (IL-4), obtained from Sigma. Cells are cultured for 5 days and then dendritic cells (DCs) harvested by centrifugation and used for experiments following verification by light microscopy examination and flow-cytometry.

DCs were infected with the virus at a multiplicity of infection (MOI) of 100. Infection experiment were carried out in polypropylene tubes to prevent the adherence of the cells. 50 $\mu$l of viral suspension were inoculated into 50 $\mu$l of cell suspension ($1.5 \times 10^6$ cells) in complete RPMI-1640 medium containing 2% of autologous serum. After inoculation the cells were incubated 90 min at 37 C. in 5% $CO_2$ at the complete RPMI-1640 medium containing 2% of autologous serum, than washed three times and incubated in RPMI-1640 medium containing 10% of autologous serum for additional 24 h at 37 C. in 5% $CO_2$. Expression of PSMA was tested by immunoblotting. Efficiency of infection of DC by the adenovirus in our experiments was 20% i.e. 20% of the DC were infected by the recombinant adenovirus.

In additional experiments DCs were obtained from HLA-A2+ patients, infected with adenovirus, and cultured with autologous T cells in CM for 3 days at 37° C. T cells were harvested at the end of the incubation, CD8+ T cells purified by negative depletion with anti-CD4 antibodies and complement and their cytotoxicity tested. The CD8+ T cells that had been stimulated by autologous DC infected with Ad5-PSMA were cytotoxic against the prostate tumor cell line LNCaP.FGC (also of the HLA A2+ phenotype), but not against Jurkat (T leukemia) or U937 (myelomonocytic cell line) cells. In comparison, freshly separated T cells showed no cytotoxicity against any of the three cell lines.

In vivo experiments:
Patient Treatment with Plasmid or Adenovirus
Study Design

One group of seven patients received three injections of XC PSMA-DNA vaccine (XC PSMA-CD86 plasmid) at the same dose (100 ug) at one-week intervals. Five patients (see table 1) received 10,000 IU Leukine (Immunex, Seattle, Wash. at the site of the plasmid application immediately or 24 and 48 hours after the immunization.

Additionally, two months later, these seven patients and a group of 2 new patients received three injections of a recombinant, replication-deficient adenoviral (Ad5-XC-PSMA) vaccine ($5 \times 10^8$ PFUs per application) at one-week intervals.

Plasmid was injected intradermally between the first and second toe of the right leg or intramuscularly. The viral vaccine was administered intradermally in the navel area.

Constant monitoring of the clinical state and the vital signs was carried out for 2 hours after vaccination. If stable, the subject was allowed to leave the hospital. A brief follow-up visit occurred 24 (and 48 in the case of GM-CSF innoculation) hours later.

Inclusion Criteria

All patients signed an informed consent form before admission into the study. Data from monitoring visits were shared with the patients as the study proceeded, and the patients were reminded that hey were free to withdraw from participation at any time. Only patients with advanced, hormone-resistant cancer or patients unable to find or administer hormone therapy were included into the study.

Patients with a history of another malignancy or with a serious active infection or with another illness were excluded from the study.

Monitoring Studies

Standard laboratory tests included CBC, urinanalysis, liver enzymes, antinuclear antibodies, erythrocyte sedimentation rate, PSA. Each patient had a pelvic CAT scan, chest radiograph and a cardiograph on entry and on week 20 (week 10 for the 2 patients immunized with virus only). Safety was defined as lack of untoward clinical or laboratory events, with particular attention to local and systemic reactions, as well evidence of anti-nuclear antibody.

Additionally, analysis of CD/HLA $DR^+$; $CD4^+$; $CD8^+$; $CD3^-/CD16^+CD56^+$; $CD3^+$; $CD1^+$; $CD25^+$; $CD19^+$ cells as well as CD4/CD8 ratio prior and following immunotherapy was performed by flow cytometry.

Results
Characteristics of Participants

Nine men, ages between 49 and 69 with advanced adenocarcinoma of the prostate, were included in the study. Three patients had a radical prostatectomy, 2 were in preparation for surgery, three were inoperable and one was operable but had other contraindications for surgery treatment. Two of the patients died due to advanced cancer disease.

Safety monitoring results

The immunizations were well tolerated. No changes in vital signs occurred following injections or on follow-up visits.

Patients who received intradermal immunizations with plasmid had a minor DTH-like reactions 24 hours following the third immunization. Patients NN 8 and 9 developed a DTH reaction 24 hours following each administration of the recombinant adenovirus. Patients NN 1 through 7 had no DTH-like reactions 24 hrs after the first immunization with the viral vector, but developed DTH after the second and third immunization. All DTH-like local reactions were mild and resolved within 72-hrs post immunization.

Patient N 4 had a vesicular rash after the last viral immunization which was located on the back and which resolved in the next two days with no treatment.

Patient N 7 had a papular urticaria-like rash with small petechiae at the center which developed 24 hrs after the last plasmid immunization and which disappeared after the discontinuation of the antibiotic therapy he was receiving.

No significant changes occurred in erythrocyte sedimentation rate, CBC, serum creatinine or other blood chemistries, or urinanalysis. Serum liver chemistry values remained within normal range in all subjects.

No significant changes in the analysis of CD/HLA $DR^+$; $CD4^+$; $CD8^+$; $CD3^-/CD16^+CD56^+$; $CD3^+$; $CD1^+$; $CD25^+$; $CD19^+$ cells as well as CD4/CD8 ratio prior and following immunotherapy were detected.

No subject developed abnormal vital signs following injection, no significant increase in antinuclear antibodies titer were observed, and anti-DNA antibody was not detected.

For PSA values, CAT-scans, bone scintigraphy or lymph node metastases before and after immunization see tables 1 and 2.

Tables 1 and 2 show that in some patients the progression of metastatic prostate cancer was retarded or stopped.

TABLE 1

Patients were immunized initially three times at weekly intervals with PSMA plasmid. Two months later all patients but patient #7 received three additional immunizations at weekly intervals with the recombinant adenovirus.

| Patient # | Stage of disease | Type of immunization | Additional treatment | PSA(ng/ml) before | PSA(ng/ml) after | CT scan before | CT scan after | LN before | LN after | Bone metastases | Side effects |
|---|---|---|---|---|---|---|---|---|---|---|---|
| 1 | $T_4 N_X M_2$ inoperable | 3× plsmd i.d. 3 × Ad5PSMA | orchiectomy Casodex | 6.3 | – | +++ | +++ | – | + | ++ ++ | exitus |
| 2 | $T_2N_0M_0$ operable# | 3× plsmd i.m. +GM-CSF 3 × Ad5PSMA | orchiectomy Androcur | 14.38 | 0.28 | +++ | * | – | – | – – | none |
| 3 | $T_4N_XM_0$ inoperable | 3× plsmd i.d. 3 × Ad5PSMA | orchiectomy | 33.0 | 0.04 | +++ | * | – | – | – + | none |
| 4 | $T_4M_XM_2$ post BPH and TUR inoperable | 3× plsmd i.d. +GM-CSF 3 × Ad5PSMA | orchiectomy (recently Flucinome) | 1.11 | 3.8 | ++ | ++ | – | – | + ++ | none |

TABLE 1-continued

Patients were immunized initially three times at weekly intervals with PSMA plasmid.
Two months later all patients but patient #7 received three additional immunizations at weekly
intervals with the recombinant adenovirus.

| Patient # | Stage of disease | Type of immunization | Additional treatment | PSA(ng/ml) before | PSA(ng/ml) after | CT scan before | CT scan after | LN before | LN after | Bone metastases | Side effects |
|---|---|---|---|---|---|---|---|---|---|---|---|
| 5 | $T_{2-3}N_0M_0$ in preparation for surgery | 3× plsmd i.d +GM-CSF 3 × Ad5PSMA | MAB | 3.01 | 0.05 | ++ | * | – | – | – | none |
| 6 | $T_{3-4}N_XM_X$ post TUR | 3× plsmd i.d. +GM-CSF 3 × Ad5PSMA | orchiectomy MAB | 1.6 | 0.04 | +++ | * | – | – | – | none |
| 7 | $T_4N_XM_2$ post radical prostatectomy metastases | 3× plsmd i.m. +GM-CSF | MAB | 100 | | +++ | ++** | – | | ++ | exitus skin rash *** |

Legend:
++; +++ increase in the size of the prostate gland or presence of metastatic tumor post radical prostatectomy (patient #7)
–; + lack (–) or presence of bone metastases or lymph node engagement
* significant decrease in the size of the prostate gland.
**- Patient #7. Lack of urine excretion from both urethers due to metastases prior to the immune therapy. Appearance of diuresis from the right kidney one month after the last immunization. Died due to mechanical illeus following blockade of the rectum and sigmoideum by metastases.
***- Patient #7 had a mild skin rash 24 hrs post the third plasmid application which disappeared after discontinuation of the concurrent antibiotic therapy.
- Patient #2 could not have surgery due to cardiovascular complications.
MAB- maximum androgen blockade with Zoladex, Casodex or Flucinome orchiectomy-always bilateral

TABLE 2

Patients who were immunized with recombinant adenovirus 3 times at weekly intervals.

| Patient # | Stage of disease | Type of immunization | Additional treatment | PSA(ng/ml) before | PSA(ng/ml) after | CT scan before | CT scan after | LN before | LN after | Bone metastases | Side effects |
|---|---|---|---|---|---|---|---|---|---|---|---|
| 8 | $T_4N_{2M}$ post radical prostatectomy metastases | 3 × Ad5PSMA | MAB | 32 | NA | +++ | NA | +++ | NA | – | NA none |
| 9 | $T_4NM_2$ post radical prostatectomy metastases | 3 × Ad5PSMA | MAB | 4.47 | NA | +++ | NA | – | NA | +++ | NA none |

–; ++; +++ lack (–) or presence of local tumor metastases, or lymph node engagement
MAB- maximum androgen blockade with Zoladex, Casodex or Flucinome
NA- not available It will be apparent to those skilled in the art that the examples and embodiments described herein are by way of illustration and not of limitation, and that other examples may be used without departing from the spirit and scope of the present invention, as set forth in the claims.

We claim:

1. A method for treating prostate cancer in a subject comprising administering to a subject having prostate cancer an effective amount of a polynucleotide operably linked to a promoter, which polynucleotide encodes a truncated form of human prostate specific membrane antigen (PSMA) comprising the extracellular domain and lacking functional transmembrane and cytoplasmic domains; to thereby destroy malignant prostate cells in the subject and thereby treat the prostate cancer in the subject.

2. The method of claim 1, wherein the truncated form of human PSMA lacks the transmembrane and cytoplasmic domains.

3. The method of claim 2, wherein the truncated form of human PSMA consists of the extracellular domain of human PSMA comprising SEQ ID NO: 1.

4. The method of claim 1, wherein the polynucleotide is included in a plasmid.

5. The method of claim 4, wherein the plasmid consists of the plasmid having ATCC Accession No. 203168.

6. The method of claim 1, wherein the polynucleotide is included in a viral vector.

7. The method of claim 6, wherein the viral vector is an adenovirus.

8. The method of claim 7, wherein the adenovirus is a replication-deficient adenovirus.

9. The method of claim 1, further comprising waiting for an appropriate time after the administration, and administering to the subject a second dose of a polynucleotide operably linked to a promoter, which polynucleotide encodes a truncated form of human PSMA comprising the extracellular domain and lacking functional transmembrane and cytoplasmic domains.

10. The method of claim 4, further comprising waiting for an appropriate time after the administration, and administering to the subject a dose of a viral vector encoding a truncated form of human PSMA comprising the extracellular domain and lacking functional transmembrane and cytoplasmic domains.

11. The method of claim 10, wherein the plasmid and the viral vector encode a truncated form of human PSMA comprising SEQ ID NO: 1.

12. The method of claim 6, further comprising waiting for an appropriate time after the administration, and administering to the subject a dose of a plasmid encoding a truncated form of human PSMA comprising the extracellular domain and lacking functional transmembrane and cytoplasmic domains.

13. The method of claim 12, wherein the viral vector and the plasmid encode a truncated form of PSMA comprising SEQ ID NO: 1.

14. The method of claim 9, further comprising waiting for an appropriate time after the administration of the second dose, and administering to the subject a third dose of a polynucleotide operable linked to a promoter, which polynucleotide encodes a truncated form of human PSMA comprising the extracellular domain and lacking functional transmembrane and cytoplasmic domains.

15. The method of claim 8, wherein the adenovirus consists of the adenovirus having ATCC Accession No. VR2631.

16. The method of claim 9, wherein the two doses are administered at about a one-week interval.

17. The method of claim 14, wherein the three doses are administered at about one-week intervals.

18. The method of claim 10, wherein the viral vector is administered about two months after administration of the plasmid.

19. The method of claim 12, wherein the plasmid is administered about two months after administration of the vector.

20. The method of claim 10, wherein two doses of a plasmid are administered to the subject before administering two doses of a viral vector, wherein the plasmid and the viral vector encode a truncated form of PSMA comprising the extracellular domain and lacking functional transmembrane and cytoplasmic domains.

21. The method of claim 20, wherein the two doses of plasmid are administered to the subject at about a one-week interval; the two doses of viral vector are administered to the subject at about a one-week interval; and the first dose of the viral vector is administered about two months after the second dose of the plasmid.

22. The method of claim 21, wherein the truncated form of PSMA is a truncated form of PSMA comprising SEQ ID NO: 1.

23. The method of claim 1, further comprising administering to the subject a polynucleotide encoding CD86.

24. The method of claim 23, wherein the polynucleotide encoding the truncated form of PSMA and the polynucleotide encoding CD86 are included in a single plasmid or vector.

25. The method of claim 1, wherein the polynucleotide is administered intradermally.

26. The method of claim 1, wherein the polynucleotide is administered intramuscularly.

27. The method of claim 1, wherein granulocyte-macrophage colony stimulating factor (GM-CSF) is administered to the subject.

28. The method of claim 20, further comprising administering GM-CSF to the subject after administrating the plasmid.

29. The method of claim 20, further comprising administering GM-CSF to the subject simultaneously with the administration of the plasmid.

30. The method of claim 28, further comprising administrating to the subject a polynucleotide encoding CD86.

* * * * *

SEQUENCE LISTING (1) GENERAL INFORMATION:

(iii) NUMBER OF SEQUENCES: 1

(2) INFORMATION FOR SEQ ID NO: 1:

(i) SEQUENCE CHARACTERISTICS:
        (A) LENGTH: 2133 base pairs
        (B) TYPE: nucleic acid
        (C) STRANDEDNESS: double
        (D) TOPOLOGY: linear (ii) MOLECULE TYPE: cDNA (iii) HYPOTHETICAL: no (iv) ANTI-SENSE: no (vi) ORIGINAL SOURCE:
         (A) ORGANISM: human
         (G) CELL TYPE: prostate cell line LNCaP
         (B) CLONE: Molecular cloning of a complimentary DNA encoding a
             prostate-specific membrane antigen.

(x) PUBLICATION INFORMATION:
         (A) AUTHORS: Israeli, R.S., Powell, C.T., Fair, W.R.,
             Murphy, G.P.

(xi) SEQUENCE DESCRIPTION: SEQ ID NO: 1:

```
ATG AAA TCC TCC AAT GAA GCT ACT AAC ATT ACT CCA AAG CAT AAT              45
Met Lys Ser Ser Asn Glu Ala Thr Asn Ile Thr Pro Lys His Asn
1               5                  10                  15

ATG AAA GCA TTT TTG GAT GAA TTG AAA GCT GAG AAC ATC AAG AAG              90
Met Lys Ala Phe Leu Asp Glu Leu Lys Ala Glu Asn Ile Lys Lys
                20                  25                  30

TTC TTA TAT AAT TTT ACA CAG ATA CCA CAT TTA GCA GGA ACA GAA             135
Phe Leu Tyr Asn Phe Thr Gln Ile Pro His Leu Ala Gly Thr Glu
                35                  40                  45

CAA AAC TTT CAG CTT GCA AAG CAA ATT CAA TCC CAG TGG AAA GAA             180
Gln Asn Phe Gln Leu Ala Lys Gln Ile Gln Ser Gln Trp Lys Glu
                50                  55                  60

TTT GGC CTG GAT TCT GTT GAG CTA GCA CAT TAT GAT GTC CTG TTG             225
Phe Gly Leu Asp Ser Val Glu Leu Ala His Tyr Asp Val Leu Leu
                65                  70                  75

TCC TAC CCA AAT AAG ACT CAT CCC AAC TAC ATC TCA ATA ATT AAT             270
Ser Tyr Pro Asn Lys Thr His Pro Asn Tyr Ile Ser Ile Ile Asn
                80                  85                  90

GAA GAT GGA AAT GAG ATT TTC AAC ACA TCA TTA TTT GAA CCA CCT             315
Glu Asp Gly Asn Glu Ile Phe Asn Thr Ser Leu Phe Glu Pro Pro
                95                 100                 105

CCT CCA GGA TAT GAA AAT GTT TCG GAT ATT GTA CCA CCT TTC AGT             360
Pro Pro Gly Tyr Glu Asn Val Ser Asp Ile Val Pro Pro Phe Ser
               110                 115                 120

GCT TTC TCT CCT CAA GGA ATG CCA GAG GGC GAT CTA GTG TAT GTT             405
Ala Phe Ser Pro Gln Gly Met Pro Glu Gly Asp Leu Val Tyr Val
               125                 130                 135

AAC TAT GCA CGA ACT GAA GAC TTC TTT AAA TTG GAA CGG GAC ATG             450
Asn Tyr Ala Arg Thr Glu Asp Phe Phe Lys Leu Glu Arg Asp Met
               140                 145                 150

AAA ATC AAT TGC TCT GGG AAA ATT GTA ATT GCC AGA TAT GGG AAA             495
Lys Ile Asn Cys Ser Gly Lys Ile Val Ile Ala Arg Tyr Gly Lys
               155                 160                 165

GTT TTC AGA GGA AAT AAG GTT AAA AAT GCC CAG CTG GCA GGG GCC             540
Val Phe Arg Gly Asn Lys Val Lys Asn Ala Gln Leu Ala Gly Ala
               170                 175                 180

AAA GGA GTC ATT CTC TAC TCC GAC CCT GCT GAC TAC TTT GCT CCT             585
Lys Gly Val Ile Leu Tyr Ser Asp Pro Ala Asp Tyr Phe Ala Pro
               185                 190                 195

GGG GTG AAG TCC TAT CCA GAT GGT TGG AAT CTT CCT GGA GGT GGT             630
Gly Val Lys Ser Tyr Pro Asp Gly Trp Asn Leu Pro Gly Gly Gly
               200                 205                 210

GTC CAG CGT GGA AAT ATC CTA AAT CTG AAT GGT GCA GGA GAC CCT             675
Val Gln Arg Gly Asn Ile Leu Asn Leu Asn Gly Ala Gly Asp Pro
               215                 220                 225

CTC ACA CCA GGT TAC CCA GCA AAT GAA TAT GCT TAT AGG CGT GGA             720
```

```
Leu Thr Pro Gly Tyr Pro Ala Asn Glu Tyr Ala Tyr Arg Arg Gly
            230                 235                 240

ATT GCA GAG GCT GTT GGT CTT CCA AGT ATT CCT GTT CAT CCA ATT      765
Ile Ala Glu Ala Val Gly Leu Pro Ser Ile Pro Val His Pro Ile
            245                 250                 255

GGA TAC TAT GAT GCA CAG AAG CTC CTA GAA AAA ATG GGT GGC TCA      810
Gly Tyr Tyr Asp Ala Gln Lys Leu Leu Glu Lys Met Gly Gly Ser
            260                 265                 270

GCA CCA CCA GAT AGC AGC TGG AGA GGA AGT CTC AAA GTG CCC TAC      855
Ala Pro Pro Asp Ser Ser Trp Arg Gly Ser Leu Lys Val Pro Tyr
            275                 280                 285

AAT GTT GGA CCT GGC TTT ACT GGA AAC TTT TCT ACA CAA AAA GTC      900
Asn Val Gly Pro Gly Phe Thr Gly Asn Phe Ser Thr Gln Lys Val
            290                 295                 300

AAG ATG CAC ATC CAC TCT ACC AAT GAA GTG ACA AGA ATT TAC AAT      945
Lys Met His Ile His Ser Thr Asn Glu Val Thr Arg Ile Tyr Asn
            305                 310                 315

GTG ATA GGT ACT CTC AGA GGA GCA GTG GAA CCA GAC AGA TAT GTC      990
Val Ile Gly Thr Leu Arg Gly Ala Val Glu Pro Asp Arg Tyr Val
            320                 325                 330

ATT CTG GGA GGT CAC CGG GAC TCA TGG GTG TTT GGT GGT ATT GAC     1035
Ile Leu Gly Gly His Arg Asp Ser Trp Val Phe Gly Gly Ile Asp
            335                 340                 345

CCT CAG AGT GGA GCA GCT GTT GTT CAT GAA ATT GTG AGG AGC TTT     1080
Pro Gln Ser Gly Ala Ala Val Val His Glu Ile Val Arg Ser Phe
            350                 355                 360

GGA ACA CTG AAA AAG GAA GGG TGG AGA CCT AGA AGA ACA ATT TTG     1125
Gly Thr Leu Lys Lys Glu Gly Trp Arg Pro Arg Arg Thr Ile Leu
            365                 370                 375

TTT GCA AGC TGG GAT GCA GAA GAA TTT GGT CTT CTT GGT TCT ACT     1170
Phe Ala Ser Trp Asp Ala Glu Glu Phe Gly Leu Leu Gly Ser Thr
            380                 385                 390

GAG TGG GCA GAG GAG AAT TCA AGA CTC CTT CAA GAG CGT GGC GTG     1215
Glu Trp Ala Glu Glu Asn Ser Arg Leu Leu Gln Glu Arg Gly Val
            395                 400                 405

GCT TAT ATT AAT GCT GAC TCA TCT ATA GAA GGA AAC TAC ACT CTG     1260
Ala Tyr Ile Asn Ala Asp Ser Ser Ile Glu Gly Asn Tyr Thr Leu
            410                 415                 420

AGA GTT GAT TGT ACA CCG CTG ATG TAC AGC TTG GTA CAC AAC CTA     1305
Arg Val Asp Cys Thr Pro Leu Met Tyr Ser Leu Val His Asn Leu
            425                 430                 435

ACA AAA GAG CTG AAA AGC CCT GAT GAA GGC TTT GAA GGC AAA TCT     1350
Thr Lys Glu Leu Lys Ser Pro Asp Glu Gly Phe Glu Gly Lys Ser
            440                 445                 450

CTT TAT GAA AGT TGG ACT AAA AAA AGT CCT TCC CCA GAG TTC AGT     1395
Leu Tyr Glu Ser Trp Thr Lys Lys Ser Pro Ser Pro Glu Phe Ser
            455                 460                 465

GGC ATG CCC AGG ATA AGC AAA TTG GGA TCT GGA AAT GAT TTT GAG     1440
Gly Met Pro Arg Ile Ser Lys Leu Gly Ser Gly Asn Asp Phe Glu
            470                 475                 480

GTG TTC TTC CAA CGA CTT GGA ATT GCT TCA GGC AGA GCA CGG TAT     1485
Val Phe Phe Gln Arg Leu Gly Ile Ala Ser Gly Arg Ala Arg Tyr
            485                 490                 495

ACT AAA AAT TGG GAA ACA AAC AAA TTC AGC GGC TAT CCA CTG TAT     1530
Thr Lys Asn Trp Glu Thr Asn Lys Phe Ser Gly Tyr Pro Leu Tyr
            500                 505                 510

CAC AGT GTC TAT GAA ACA TAT GAG TTG GTG GAA AAG TTT TAT GAT     1575
His Ser Val Tyr Glu Thr Tyr Glu Leu Val Glu Lys Phe Tyr Asp
            515                 520                 525
```

-continued

| | | | | | | | | | | | | |
|---|---|---|---|---|---|---|---|---|---|---|---|---|
| CCA | ATG | TTT | AAA | TAT | CAC | CTC | ACT | GTG | GCC | CAG | GTT | CGA | GGA | GGG | 1620 |
| Pro | Met | Phe | Lys | Tyr | His | Leu | Thr | Val | Ala | Gln | Val | Arg | Gly | Gly | |
| | | | 530 | | | | | 535 | | | | | | 540 | |
| ATG | GTG | TTT | GAG | CTA | GCC | AAT | TCC | ATA | GTG | CTC | CCT | TTT | GAT | TGT | 1665 |
| Met | Val | Phe | Glu | Leu | Ala | Asn | Ser | Ile | Val | Leu | Pro | Phe | Asp | Cys | |
| | | | | 545 | | | | | 550 | | | | | 555 | |
| CGA | GAT | TAT | GCT | GTA | GTT | TTA | AGA | AAG | TAT | GCT | GAC | AAA | ATC | TAC | 1710 |
| Arg | Asp | Tyr | Ala | Val | Val | Leu | Arg | Lys | Tyr | Ala | Asp | Lys | Ile | Tyr | |
| | | | | | 560 | | | | | 565 | | | | 570 | |
| AGT | ATT | TCT | ATG | AAA | CAT | CCA | CAG | GAA | ATG | AAG | ACA | TAC | AGT | GTA | 1755 |
| Ser | Ile | Ser | Met | Lys | His | Pro | Gln | Glu | Met | Lys | Thr | Tyr | Ser | Val | |
| | | | | | 575 | | | | | 580 | | | | | 585 |
| TCA | TTT | GAT | TCA | CTT | TTT | TCT | GCA | GTA | AAG | AAT | TTT | ACA | GAA | ATT | 1800 |
| Ser | Phe | Asp | Ser | Leu | Phe | Ser | Ala | Val | Lys | Asn | Phe | Thr | Glu | Ile | |
| | | | | | | 590 | | | | | 595 | | | | 600 |
| GCT | TCC | AAG | TTC | AGT | GAG | AGA | CTC | CAG | GAC | TTT | GAC | AAA | AGC | AAC | 1845 |
| Ala | Ser | Lys | Phe | Ser | Glu | Arg | Leu | Gln | Asp | Phe | Asp | Lys | Ser | Asn | |
| | | | | | | 605 | | | | | 610 | | | | 615 |
| CCA | ATA | GTA | TTA | AGA | ATG | ATG | AAT | GAT | CAA | CTC | ATG | TTT | CTG | GAA | 1890 |
| Pro | Ile | Val | Leu | Arg | Met | Met | Asn | Asp | Gln | Leu | Met | Phe | Leu | Glu | |
| | | | | | 620 | | | | | 625 | | | | | 630 |
| AGA | GCA | TTT | ATT | GAT | CCA | TTA | GGG | TTA | CCA | GAC | AGG | CCT | TTT | TAT | 1935 |
| Arg | Ala | Phe | Ile | Asp | Pro | Leu | Gly | Leu | Pro | Asp | Arg | Pro | Phe | Tyr | |
| | | | | | | 635 | | | | | 640 | | | | 645 |
| AGG | CAT | GTC | ATC | TAT | GCT | CCA | AGC | AGC | CAC | AAC | AAG | TAT | GCA | GGG | 1980 |
| Arg | His | Val | Ile | Tyr | Ala | Pro | Ser | Ser | His | Asn | Lys | Tyr | Ala | Gly | |
| | | | | | | 650 | | | | | 655 | | | | 660 |
| GAG | TCA | TTC | CCA | GGA | ATT | TAT | GAT | GCC | CTG | TTT | GAT | ATT | GAA | AGC | 2025 |
| Glu | Ser | Phe | Pro | Gly | Ile | Tyr | Asp | Ala | Leu | Phe | Asp | Ile | Glu | Ser | |
| | | | | | | 665 | | | | | 670 | | | | 675 |
| AAA | GTG | GAC | CCT | TCC | AAG | GCC | TGG | GGA | GAA | GTG | AAG | AGA | CAG | ATT | 2070 |
| Lys | Val | Asp | Pro | Ser | Lys | Ala | Trp | Gly | Glu | Val | Lys | Arg | Gln | Ile | |
| | | | | | | 680 | | | | | 685 | | | | 690 |
| TAT | GTT | GCA | GCC | TTC | ACA | GTG | CAG | GCA | GCT | GCA | GAG | ACT | TTG | AGT | 2115 |
| Tyr | Val | Ala | Ala | Phe | Thr | Val | Gln | Ala | Ala | Ala | Glu | Thr | Leu | Ser | |
| | | | | | | 695 | | | | | 700 | | | | 705 |
| GAA | GTA | GCC | GGG | CCC | TAA | | | | | | | | | | 2133 |
| Glu | Val | Ala | Gly | Pro | | | | | | | | | | | |
| | | | | | 710 | | | | | | | | | | |